(12) United States Patent
Chiou

(10) Patent No.: US 8,513,225 B2
(45) Date of Patent: Aug. 20, 2013

(54) COMPOSITION AND METHOD FOR TOPICAL TREATMENT OF SKIN LESIONS

(75) Inventor: Win L Chiou, Burr Ridge, IL (US)

(73) Assignee: Winlind Skincare, LLC, Burr Ridge, IL (US)

(*) Notice: Subject to any disclaimer, the term of this patent is extended or adjusted under 35 U.S.C. 154(b) by 0 days.

(21) Appl. No.: 13/079,964

(22) Filed: Apr. 5, 2011

(65) Prior Publication Data

US 2011/0183011 A1 Jul. 28, 2011

Related U.S. Application Data

(63) Continuation-in-part of application No. 12/244,924, filed on Oct. 3, 2008.

(51) Int. Cl.
*A61K 31/047* (2006.01)
*A61K 31/765* (2006.01)
*A61K 47/10* (2006.01)

(52) U.S. Cl.
USPC ........... 514/164; 514/159; 514/738; 514/852; 514/859; 514/863; 514/772.4; 514/884; 514/944; 514/941; 24/401

(58) Field of Classification Search
USPC ................. 514/159, 164, 738, 852, 859, 863, 514/772.4, 844, 944, 941; 424/78.02, 401
See application file for complete search history.

(56) References Cited

U.S. PATENT DOCUMENTS

| | | | |
|---|---|---|---|
| 4,767,750 A | 8/1988 | Jacquet | |
| 4,883,660 A * | 11/1989 | Blackman et al. | 514/171 |
| 5,525,635 A | 6/1996 | Moberg | |
| 5,549,888 A | 8/1996 | Venkateswaran | |
| 5,569,651 A | 10/1996 | Garrison | |
| 5,667,790 A | 9/1997 | Sellers, Jr. | |
| 5,753,637 A | 5/1998 | Fried | |
| 6,455,065 B1 | 9/2002 | Hymes | |
| 6,616,923 B1 | 9/2003 | Chiou | |
| 7,201,914 B2 | 4/2007 | Dees | |
| 7,258,875 B2 | 8/2007 | Chiou | |
| 7,691,419 B2 | 4/2010 | DiLeva | |
| 2010/0087403 A1 | 4/2010 | Chiou | |
| 2010/0203107 A1 | 8/2010 | Koo et al. | |

OTHER PUBLICATIONS

AcneFree Severe with Time-Released 10% Benzoyl Peroxide & Retinol University Medical Pharmaceuticals, (Brochure are photocopies of their outside package purchased from a local drug store in Sep. 2008).

Carreira et al., Journal of Applied Oral Science, 15:5, 453-458, 2007.
Chirife et al, Antimicrobial Agents and Chemotherapy, 24:3, 409-412, 1983.
Gupta et al., JEADV, 19, 273-285, 2005.
Habif, Clinical Dermatology, 5:171-173, 8:280-281, 2010.
Habif, Clinical Dermatology, 12:454-463, 2010.
Handbook of Nonprescription Drugs, An Interactive Approach to Self-Care, 13th Edition, Section VIII, Dermatologic Disorder, ACNE, Chapter 32, 777-791, 2002.
International Cosmetic Ingredient Dictionary and handbook, Tenth Edition, vol. 2, 1536, 2004.
Johnson & Johnson, Clean & Clear advantage acne control kit, (Brochure are photocopies of their outside package purchased from a local drug store in Sep. 2008).
Katsambas et al, Dermatologic Therapy, 21: 86-95, 2008.
Remington: The Science and Practice of Pharmacy, Gennaro (Editor), 20th edition, 1205, 2000.
Rodan et al, Proactiv Solution: Take action today, Three Simple Steps to a clearer tomorrow.
Sherman, Article Propylene Glycol: The Good, the Bad, and the Alternatives, posted at http://www.naturalnews.com/023138_propylene_glycol_food_health.html Apr. 30, 2008.
International Search Report mailed May 6, 2010—International Application No. PCT/US2009/058607.
Written Opinion mailed May 6, 2010—International Application No. PCT/US2009/058607.
International Preliminary Report issued Apr. 5, 2011—International Application No. PCT/US2009/058607.
U.S. Appl. No. 12/244,924, filed Oct. 3, 2008—Pending claims filed Jun. 14, 2011.
Selected Prosecution Documents from U.S. Appl. No. 12/244,924: (1) Jun. 24, 2011 Advisory Action; (2) Jun. 15, 2011 Final Rejection; (3) Jan. 19, 2011 Examiner Interview Summary; (4) Jun. 16, 2010 Examiner Interview Summary; (5) Nov. 24, 2010 Examiner Interview Summary; (6) Oct. 1, 2010 Non-Final Rejection; (7) Jun. 23, 2010 Restriction Requirement.

* cited by examiner

*Primary Examiner* — Savitha Rao
(74) *Attorney, Agent, or Firm* — Merchant & Gould PC

(57) ABSTRACT

Disclosed herein is a composition containing a high concentration of PG is unexpectedly capable of quickly killing other bacteria, fungi, and/or virus in vitro that is indicative of its potential high efficacy in treating various skin infection. Embodiments disclosed herein relate to a composition and method for effective topical treatment of inflammatory skin lesions in mammals, comprising of a high concentration of propylene glycol alone, or in combination with an astringent. The PG at high concentrations can be regarded as an extremely effective, safe, topical, universal, microbicide.

7 Claims, No Drawings

COMPOSITION AND METHOD FOR TOPICAL TREATMENT OF SKIN LESIONS

PRIORITY

This application is a continuation-in-part of U.S. patent application Ser. No. 12/244,924, filed on Oct. 3, 2008, the subject matter of which is incorporated by reference in its entirety.

FIELD OF THE INVENTION

The invention relates to an unexpected discovery that propylene glycol (PG) is highly effective at killing or inhibiting *Propionibacterium* acnes in a mammalian skin disorder, as well as to the use of propylene glycol and salicylic acid in a skin-disorder treatment. It has also been unexpectedly found that a composition containing a high concentration of PG is capable of very quickly killing other bacteria, fungi, and/or virus. This invention also relates to compositions containing propylene glycol alone or in combination with salicylic acid for use in killing or inhibiting *Propionibacterium* acnes. The invention also relates to a composition and method for topical treatment of skin lesions in mammals, comprising of a high concentration of propylene glycol alone, or in combination with an astringent.

BACKGROUND OF THE INVENTION

Acne is a common skin disorder. Many topical and systemic treatment methods are available ("Handbook of Nonprescription Drugs," American Pharmaceutical Association, 2002, pages 777-791; Katsambas and Dessiniot, Dermatologic Therapy, 21:86-95, 2008). A major shortcoming of the current treatment methods is their slow response often requiring several months of daily application or administration. Furthermore, satisfactory results achieved are often only about 40% to 60% (Chiou, 2007, U.S. Pat. No. 7,258,875 B2). Multiple (3 to 4) treatment steps are often required. Skin dryness and irritation are common; pitting or scarring may occur after treatment. Serious adverse effects can also occur for potent drugs. Although natural polyvalent metal compounds are recently employed to treat acne (Chiou, 2007, U.S. Pat. No. 7,258,875 B2), the stickiness of products due to the glycerin and thickening agent employed is a major drawback not acceptable by many patients in spite of their efficacy (unpublished observation). This is also the case in treating rosacea (Chiou, 2007, U.S. Pat. No. 7,258,875 B2).

The above review indicates a need to develop a new, cosmetically-acceptable, simple, one-step, highly safe and highly effective method for topically treating acne and rosacea without scarring and pitting. Ideally, the new drug treatment may not require a prescription and the same preparation can be used to treat both disorders. The disclosed embodiments are aimed to achieve the above objectives. This is made possible by a surprising discovery that a commonly used, highly safe and rapidly absorbed (unpublished observation) compound possesses a strong in vitro bactericidal activity against *Propionibacterium* acnes, that is mainly responsible for the infection in acne. Many other factors are known to contribute to the occurrence of acne and vastly different approaches have been used to tackle the acne disorder. Interestingly, the same compound can also be used to treat infection in rosacea.

Infection-related skin lesions often involve inflammation, redness, swelling, pain, pus formation, itch, irritation, ruptures, wounds, or a combination of any of the above. Infections are caused by microbes, including gram-positive and gram-negative bacteria, viruses, and fungi. Identification of pathogenic microorganisms is preferred prior to anti-microbial therapy (Clinical Dermatology, 2010 by T. P. Habif, Mosby, pp. 454-463). This is because certain microbes only respond to specific antimicrobials. Also, mixed microbes, such as bacteria and fungi, may be present at the same lesion site, hence requiring different antimicrobials for treatment. Emergence of drug resistance further complicates the treatment. In the last several decades, intensive worldwide research has been conducted to discover new topical antibacterial, anti-viral, or anti-fungal compounds that are safe in vivo for treating infections; they are different from those compounds used in vitro as disinfectants or for surface sterilization, which do not need to be quickly absorbed, and have lower safety requirements.

It is believed to date that no country has ever approved a compound that can treat topical bacterial, viral, and fungal skin infections, and no single commercial topical product is available that alone can treat these infections. Any new antimicrobial is likely to be expensive and has potential serious, adverse effects. The above discussion indicates a need for an effective, safe, inexpensive compound or composition for killing in vivo a wide variety of bacteria, viruses, and fungi in skin lesions.

Disclosed herein is the surprising discovery that high concentrations of propylene glycol (PG) can be used as a microbicide to effectively treat topical lesions involving bacteria, viruses, and/or fungi (Examples 1-7). Results of in vitro studies (Example 8) appear to support the above contention. PG is relatively inexpensive and is generally regarded as safe by the FDA. PG has been commonly used in the last century in skincare products as a humectant and solvent at generally low concentrations (one to a few percent). It is believed that no commercial product for treating skin infections can show such dramatic killing effect, such as more than 99.9% of microbes killed in less than about one minute. This is significant since many, or perhaps most antibiotics used clinically are not microbicidal; for example, tetracyclines, sulfa drugs, chloramphenicol, griseofulvin, ketoconazole, undecylenic acid, and probably all anti-viral drugs only inhibit microbial growth. Not to be bound by theory, but it is believed that PG may work by disrupting the microbial cell membrane and/or by desiccating the microbes. Thus, the microbes will unlikely develop resistance to PG, an important attribute compared to antibiotics. Another useful attribute of PG is its ability to promote tissue growth and skin firming, as disclosed in U.S. Ser. No. 12/244,924.

Although PG at relatively low concentrations is known as a food preservative that is capable of exhibiting anti-microbial activity (see U.S. Pat. No. 3,853,483), the inventor is believed to be the first to develop and market a commercial product (AcFree Skin™, which contains PG and is covered by U.S. Ser. No. 12/244,924) for use as an effective microbicide to treat any infection-related skin lesions. Past reluctance to use it to treat skin infections may be two-fold. First, there may be perceived notion that PG is poorly permeable across the skin barrier, and hence is ineffective in quickly killing microbes at infection sites. This is because other similar glycols, such as glycerin and ethylene glycol, are known to be poorly permeable. Second, in the last two or three decades, there is a movement to discourage use of PG in skincare; some products are promoted as "propylene glycol free" (See article Propylene Glycol: The Good, the Bad, and the Alternatives by Cathy Sherman, Apr. 30, 2008 posted at http ://www.naturalnews.com/023138_propylene_glycol_food_health.html)

In dermatology, combining active ingredients from two or more drug classes in one product is generally rare. For example, in treating atopic dermatitis or psoriasis, physicians often prescribe a topical steroid for inflammation, a topical antibiotic for infection, a topical antihistamine for itching, and a moisturizer for dryness or scaly skin (Clinical Dermatology, 2010, by T. P. Habif, pp. 171-173, 280-281). Such a multiple-product approach is expensive and inconvenient. Recently, a combined antiperspirant and antimicrobial composition is described (U.S. Pat. No. 7,201,914). A total of 41 antimicrobials are disclosed without specifying their advantages and limitations; for treating skin lesions only one acne example is mentioned. An herbal combination containing five volatile oils to treat a wide range of skin conditions is disclosed in U.S. Pat. No. 7,691,419. The compositions tend to be malodorous and as a result may discourage user compliance.

SUMMARY OF THE INVENTION

Propylene glycol (PG) is a colorless, odorless, sweet, light liquid. It has been widely employed for almost a century in skin-care products as a solvent, humectant, skin-conditioning agent and viscosity-decreasing agent ("International Cosmetic Ingredients Dictionary and Handbook", 2004, page 1536). It is listed as an inactive ingredient in dermatological drugs approved for marketing to date. The concentrations used generally are low ranging from about one to several percent.

An object disclosed herein is the surprising discovery that high concentrations of PG in vitro can very effectively kill *P. acnes* (Example 1), and without the need for any special prior cleansing or treatment, high (such as 20% to 80% by weight) aqueous PG solutions can virtually heal various sizes of infectious (pustular or papular) acne in about 0.5 to 2-3 days after one to several topical applications without pitting and scarring (Examples 2-4). No adverse effects were observed for solutions containing up to 75% or 80% PG (Examples 3-7). Pure (100%) PG and 90% PG solutions (Example 5) caused no noticeable adverse effects on normal skin (Example 5). Daily use of the 75% or 80% PG solution showed excellent prophylactic effect against new acne formation (Example 4). An aqueous solution containing 75% PG and 0.5% salicylic acid was highly effective against acne and rosacea without adverse reactions (Example 6).

Therefore, an object is directed to a highly effective, highly safe, method for killing and inhibiting *P. acnes* in mammalian skin disorder comprising topically applying a therapeutically effective amount of PG alone or in combination with a therapeutically effective amount of salicylic acid or other anti-acne compounds in a pharmaceutically acceptable dosage form to the area of skin disorder; one such skin disorder is acne. The above approach is also highly effective in treating rosacea.

Another object is directed to compositions and methods comprising a high concentration (about 15% to about 99% by weight) of PG alone, or in combination with an astringent, for treating skin lesions. In contrast with the conventional notion of poor permeability across the skin barrier, PG can diffuse quickly to lesions beneath diseased skin and to exert its ability to kill and/or inhibit microbes as shown by its very rapid healing of acne and herpes simplex in humans (Examples 1-7 and 9). The extremely high potency of the anti-microbial property of PG is demonstrated in vitro by the killing of 99.99% of an anaerobic bacterium (*P. acnes*), three aerobic bacteria (*P. aeruginosa, E. coli,* and *S. aureus*), two fungi (*C. albicans* and *A. niger*), and one virus (Herpes simplex) in just one minute (Example 14). Similar strong anti-microbial activity should be found for other microorganisms. In view of its clinical efficacy (Examples 8-12), PG can be regarded as a new, safe, extremely potent, universal topical in vivo microbicide for treating various inflammatory skin infections or lesions. Preferred PG concentrations range from about 20% to about 99% or about 40% to about 99% by weight.

Another object is directed to a combination of a high concentration of PG with an effective amount of an astringent, such as aluminum sulfate, in a dosage form for treating various inflammatory skin lesions that may or may not be infection-related, and that are broader in scope than the earlier two patents (Examples 15-22). Furthermore, pure chemicals are used, and they can be odorless.

Astringents are useful in skincare. They can reduce gland secretion, local edema and inflammation, and promote dryness and healing, as well as help stop bleeding (Remington: The Science and Practice of Pharmacy, 20th edition, 2000, pp. 1205). It was surprisingly discovered that metallic astringents also have analgesic (Example 17) and anti-itch (Examples 18-20) properties. Furthermore, the combination may have synergistic effect in killing microorganisms (Example 23, see U.S. Pat. No. 7,201,914). Therefore, the astringent in combination with PG provides an added means for treating various topical skin lesions.

Additive or synergistic effects for treating skin lesions can be achieved by a combination of a high concentration of PG with an effective amount of an astringent. The efficacy of such combinations is demonstrated in Examples 15-22. As disclosed herein combined compositions are highly effective and safe in treating a wide variety of common skin lesions. The compositions are prepared in a pharmaceutically acceptable dosage form and applied topically as a thin layer one to a few times a day.

DETAILED DESCRIPTION OF THE INVENTION

As used herein, the word "treatment" or "treating" refers to amelioration, healing, resolving, or prevention of skin lesions in mammals. The symptoms may include pustules, papules, nodules, cysts, inflammation, redness, irritation, discomfort, pain, itch, rash, mild wound, blisters, oozing, mild bleeding, dryness, scaly skin, or any combination of the above. It also includes helping treat the above symptoms. The "skin" also refers to nails, hair, scalp, and mucosal membrane of mouth, nose, rectum, urethra, and vagina. The phrase "effective amount" refers to the amount of PG or astringent needed to achieve therapeutic outcome. The word "prevention" refers to prophylaxis. The phrase "dosage form" includes, but not limited to: a liquid solution or mixture, suspension, lotion, emulsion, ointment, gel, cream, paste, foam, spray, patch, pad, mask, medicated bandage, powder, suppository and stick. The method to prepare a dosage form is based on standard principles and methods described in various pharmaceutical literature. The phrase "salicylic acid" refers to salicylic acid or salicylate. The dosages and formulations are prepared based on principles described in pharmaceutical literature, and may include water, glycerin, polyethylene glycol, other PG-mixable solvents, and a suspending, thickening, gelling, or emulsifying agent. Other anti-microbials, humectants, anti-inflammatory agents, wound healing compounds, astringents, absorption-enhancing and skin-conditioning compounds, preservatives, and surfactant(s), fragrances, and pH modifiers may also be added. All concentrations mentioned are based on weight.

Concentrations of PG and other ingredients described in this application, as related to the treatment of acne and rosacea, are all based on weight. The effective concentration of PG may range from about 5% to about 100%, about 8% to about 100%, about 10% to about 100%, about 15% to about 100%, about 20% to about 100%, about 25% to about 100%, about 50% to about 100%, about 10% to about 90%, about 15% to about 90%, and about 20% to about 90%, or preferably from about 25% to about 85% or from about 50% to about 90%. Use of pure (100%) PG is expected to produce the most dramatic effect of killing *P. acnes*. However, it may cause some minor skin irritation to the lesion of acne or to sensitive skin. Inclusion of some glycerin such as 5% to 20% soothes the skin and eliminates the itching and tingling caused by PG (Example 2).

The dosage form used may include a suitable amount of water, glycerin, other solvent(s), electrolyte(s), pH modifier(s), surfactant(s), absorption enhancer(s), emulsifier(s), thickener(s), fragrant(s), preservative(s), or a mixture thereof.

Although not required, the dosage form may also include one or more optional or additional anti-acne ingredients, including but not limited to salicylic acid, salicylate, benzoyl peroxide, metronidazole, erythromycin, tetracyclines and their derivatives, macrolides, clindamycin, minocycline, mecloycline, cloxycycline, azithromycin, clarithromycin, retinoids, azelaic acid, polyvalent metal compounds, picolinic acids, dapsone, anti-inflammatory compounds and astringents or a mixture thereof Salicylic acid is a Food-and-Drug-Administration-approved over-the-counter drug for treating acne because of its comedolytic property. This, and benzoyl peroxide, an anti-*P. acnes* drug, and many other ingredients (up to 30 or more) are often employed to form a 3- or 4- step treatment regime for acne. Skin dryness and irritation is a known problem associated with the above regime.

The combination of the PG and salicylic acid in a liquid solution offers many unique and important advantages such as high efficacy for both infectious (pustular or papular) and non-infectious (whiteheads and blackheads in Example 6) components of acne, very low potential for allergic and adverse effects (both compounds being natural compounds), soothing, moisturizing, smoothing and firming effect on skin (Example 7), causing no pitting and scarring, a simple one-step method or a simple "all-in-one" method, great convenience for travelers (not carrying 3 or 4 bottles) and apparent economy. Furthermore, it can be used for rosacea treatment (Example 7). Disclosed embodiments may also be useful to treat other bacterial skin infections. The concentration of salicylic acid or salicylate may range from about 0.05% to about 2% or from about 0.05% to about 3% or about 0.05% to about 6%. The dosage form may include glycerin ranging from about 5% to about 20% for skin-soothing effect (Example 2).

For killing or inhibiting *P. acnes* or for treating acne or rosacea breakouts, dosage preparation can be applied as thin layers up to several times a day to the area of lesions or prophylactically to the area that may have new breakouts later.

Therefore, disclosed embodiments provide a method for treating acne and rosacea comprising topically applying a therapeutically effective amount of propylene glycol in the absence or presence of a therapeutically effective amount of salicylic acid or other anti-acne or anti-rosacea compounds in a pharmaceutically acceptable dosage form to the area of lesion of acne or rosacea.

An embodiment is directed to a composition comprising use of a high concentration of PG for treating various infection-related skin lesions. The lesions include, but not limited to the following: bacterial infections other than acne and rosacea disclosed in U.S. patent application Ser. No. 12/244,924, fungal infections, viral infections, psoriasis, eczema, rash, blisters, burns, insect bites or infestation, itch, dermatitis, atopic dermatitis, contact dermatitis, cellulitus, folliculitis, nail infections, hair infections, scalp infections, boils, impertigo, hemorrhoids, canker sore, gingivitis, periodontitis, vaginitis, scrape, cut, surgical incision, sunburn, skin irritation, chapped lips, cracked skin, bruises, and combinations thereof. As related to the above-noted conditions (other than acne and rosacea), PG concentrations may range approximately from 15% to 99%, 20% to 99%, 25% to 99%, 30% to 99%, 35% to 99%, 40% to 99%, 45% to 99%, 50% to 99%, 55% to 99%, 60% to 99%, 65% to 99%, 70% to 99%, 75% to 99%, or 80% to 99%. A sub-aspect provides for a propylene glycol range from about 30% to about 90%, 40% to 90%, 50% to 90%, 60% to 90%, or 70% to 90%, and all integer values inbetween. Other anti-microbials ranging from 0.01% to about 20% may be added, which may include, but is not limited to conventional anti-bacterials, such as tetracyclines, aminoglycosides, penicillins and derivatives, metronidazole, ampicillins and cephalosporins; anti-fungals, such as ketoconazole, fluconazole, nystatin, terbinafine, and amphotericin; and anti-viral compounds, such as acyclovir and zidovudine. Topical steroidal anti-inflammatory compounds ranging from about 0.01% to about 3%, such as hydrocortisone, prednisone, prednisolone, triamcinolone, betamethasone and dexamethasone, may also be added. Topical non-steroidal, anti-inflammatory compounds ranging from about 0.01% to about 30%, such as salicylic acid, salicylate, acetaminophen, and ibuprofen may also be added. Any other useful agents for controlling skin lesions, such as pimecrolimus, tacrolimus, tar, tea extracts, aloevera, astringents, emollients, humectants, anesthetics and/or analgesics, may be added.

Another embodiment is directed to a composition comprising a high concentration of PG in combination with an astringent(s) for treating skin lesions. The astringents are selected from a group consisting of salts, complexes or oxides of aluminum, zinc, iron, bismuth and zirconium. They include the following non-limiting examples: aluminum sulfate, aluminum salicylate, potassium alum, aluminum acetate, aluminum ammonium sulfate, aluminum chloride, aluminum chlorohydrate, aluminum zirconium tetrachlorohydrate, aluminum zirconium tetrachlorohydrex gly, aluminum dichlorohydrex PG complex, aluminum dichlorohydrex PEG complex, aluminum chlorohydrate glycine, aluminum zirconium pentachlorohydrate, aluminum glycinate, aluminum dichlorohydrate, aluminum sesquichlorohydrate, aluminum sesquichlorohydrex PEG, aluminum sesquichlorohydrex PG, aluminum zirconium octachlorohydrate, aluminum zirconium octachlorohydrex gly, aluminum zirconium pentachlorohydrex gly, aluminum zirconium trichlorohydrate, aluminum zirconium trichlorohydrex gly, zinc chlorohydrate, zinc acetate, zinc chloride, zinc gluconate, zinc sulfate, zinc salicylate, bismuth subsalicylate, bismuth citrate, bismuth subcarbonate, bismuth subgallate, bismuth subnitrate, or combination of any of above. Ideally, the astringent used should be dissolved in the water-propylene glycol mixture. Astringent concentrations may range from about 0.01% to about 30%, about 0.05% to about 30%, about 0.1% to about 30%, about 0.2% to about 30%, about 0.5% to about 30%, about 1.0% to about 30%, about 2.0% to about 30%, about 3.0% to about 30%, about 4.0% to about 30%, or about 5.0% to about 30%. Steroidal anti-inflammatory compounds ranging from about 0.01% to about 3% and non-steroidal anti-inflammatory compounds ranging from about 0.01% to about 30% may also be added. It is understood that for all ranges recited herein that integer values inbetween said ranges are contemplated as endpoints.

In certain embodiments, the component to form a salt or complex of an astringent is required to be pharmacologically inert (such as sulfate, chloride, citrate, acetate, and glycine) or beneficial (such as salicylate in aluminum salicylate due to its anti-inflammatory property) in the treatment of skin lesions. It does not include, for example, an aluminum complex of an anti-hypertensive moiety. One of ordinary skill will appreciate that the concentration of astringents and PG used could vary with the site and nature of skin lesions. For example, concentrations greater than about 4% of astringents or 70% of PG are irritating to gum tissues, but not to warts on the skin. With the exception of bismuth, the salts or complexes used should be soluble in water, at least greater than 1%; they are herein also referred to as water-soluble salts or complexes.

The skin lesions to be treated by the above combined compositions include bacterial infection, fungal infection, viral infection, microbial infection, acne, rosacea, psoriasis, eczema, rash, blisters, burns, herpes simplex, warts, insect bites or infestation, itch, dermatitis, shingles, atopic dermatitis, contact dermatitis, cellulitus, folliculitis, nail infections, boils, hair infections, scalp infections, impertigo, hemorrhoids, canker sore, gingivitis, periodontitis, vaginitis, nose lesion, swelling, allergy, herpes zoster, cut, surgical incision, sunburn, cracked skin, bruises, and combinations thereof. It is also postulated that PG can be used as an effective microbicidal or microbiostatic agent in the preparation of antimicrobial soaps or lotions.

The disclosed embodiments are better understood by the following non-limiting examples.

EXAMPLES

Example 1

20% and 65% PG in Water for in vitro Time-Kill Studies

An aqueous solution containing 20 or 65% PG was prepared by mixing PG and water in a proper proportion for the standard time-kill study using *Propionibacterium* acnes ATCC #6919. For the 20% PG solution 47% and 98% of the bacteria were killed at one and five hours, respectively. For the 65% PG solution 91% and 99.6% of the bacteria were killed at one in and five hours, respectfully. The initial bacteria count was $1.78 \times 10^6$ CFU/mL. Much higher PG solutions are expected to produce much higher killing rates.

Example 2

80% PG in Water for Acne Treatment: A Dramatic Effect

The above aqueous PG solution was directly applied as thin layers to several infectious papular acnes in the forehead of an adult. The infection (inflammation) appeared to completely disappear in 8 hours indicating a virtual healing only after one application. On another day, a larger papular acne was also practically healed in about 8 hours after only one application without scarring and pitting. Mild itching and tingling lasting about three minutes occurred in both studies. These minor adverse effects were totally avoided when some glycerin (about 10%) was added to the mixture. No special cleansing of the lesion or skin is required for all the studies described here and below, hence it is a truly simple one-step method or "all-in-one" method.

Example 3

20%, 40% and 60% PG in Water for Acne Treatment

The above PG solutions were used to treat papular and pustular acne on the face on different occasions in a subject. Complete healing was achieved after several applications in 2 to 3 days without pitting and scarring. No itching or tingling occurred.

Example 4

75% or 80% PG Solution for Acne Treatment: A Dramatic Prophylactic Effect

An aqueous solution containing 75% PG was employed to successfully treat various sizes of pustular and papular acne in 4 adults. Daily applications were also performed in two adults for about one month without any side effects and with a clear sign of completely inhibiting new infectious acne formation indicating an excellent prophylactic effect. This was also the case with an 80% PG solution containing about 10% of glycerin.

Example 5

Daily application of 90% PG or 100% PG in Adults without Acne

Pure (100%) PG or 90% PG in water was applied repeatedly to the normal skin of face and arm in 2 adults for several days. No adverse reactions were observed.

Example 6

75% PG-0.5% Salicylic Solution for Treatment of Acne

The above PG-salicylic acid solution was applied twice a day to the area of rosacea lesion in one subject and satisfactory results to quickly control breakouts and redness were obtained. The solution was also used to very successfully treat acne in two subjects without any adverse effects. Furthermore, the solution was highly effective against whiteheads and slower in response against blackheads; a higher salicylic acid concentration should be more efficacious. The PG is an excellent solvent for salicylic acid in this preparation.

Example 7

Tissue-healing and Skin Firming Properties of PG

In all the studies conducted, PG solutions resulted in rapid healing of acne lesions without pitting and scarring. Furthermore, the applied areas of skin became smoother and firmer after about one month of daily use. These results indicate a tissue-healing and tissue-growth-promoting property of PG that is similar to the skin-firming phenomenon observed with a similar type of compound, glycerin (Chiou et al., U.S. Pat. No. 6,616,923, B1; unpublished observations).

AcFree Skin™, a commercially available composition containing greater than 50% PG in aqueous medium, was developed based on the early invention disclosed in U.S. Ser.

No. 12/244,924, and has been freely sold in U.S. over the past year. Approximately fifty dermatologists have evaluated the product, and excellent efficacy in treating inflammatory papular and pustular acne without adverse effects was observed. A similarly formulated product sold under a private label arrangement is now being sold by several major chain stores throughout the country.

Example 8

Treatment of Rosacea by AcFree Skin™ Solution

A male medical doctor, who had experienced facial rosacea for about 20 years, applied AcFree Skin™ daily for several months. The product was highly effective in controlling his inflammatory or reddish breakouts without any side effects, and was deemed by him as the best rosacea product he had ever tried.

Example 9

Dramatic Result from Treatment of Herpes Simplex

A male adult developed a typical herpes simplex lesion on his lip. After applying a hydrogel containing 80% PG (Methocel being used as a gelling agent before bedtime) once, the lesion dried overnight, indicating complete killing of the virus. The lesion healed naturally without any scarring or irritation. This result compared very favorably with reported efficacies of other commercial products that are virustatic and require many days of oral or topical applications (Habif, supra).

Example 10

Dramatic Result from Treatment of Wart by Gel, but not Solution

A male adult developed a typical filiform wart above the lip. Application of an 80% PG-20% water solution showed no effect in controlling his viral lesions; however, a gel containing 80% PG was found to be extremely effective. The lesion dried up and sloughed off after only two applications. The above result compared extremely well with those from conventional therapy (W. L. Chiou, U.S. Pat. No. 7,258,875; Habif, supra). The failure of the solution in the above treatment is apparently due to its runny property illustrating the importance of a properly formulated dosage form. See below for additional studies on warts.

Example 11

Treatment of Canker Sore by a PG Gel: Partial Effectiveness

An 80% PG hydrogel was prepared and applied to a prodromal lesion on the tongue of a male adult who had frequently suffered recurrent canker sores for several decades. The pain subsided significantly, but the lesion did not completely go away, indicating partial effectiveness of the PG treatment. The effect was dramatically improved using a different formulation shown below. Although exact causes of canker sores are unknown, bacterial and viral infections have been implicated.

Example 12

Effective Treatment of Herpes Zoster with High PG Strength

A viscous mixture containing 80% PG and 1% salicylic acid was applied twice daily to lesions on the abdomen of a male adult who developed typical symptoms of herpes zoster. The lesions were completely healed in about 10 days. Presently, no topical antiviral drugs are recommended to treat herpes zoster apparently because of their poor percutaneous absorption and their weak virus-inhibiting property. The subject received no oral anti-viral drugs.

Example 13

Rapid Penetration of PG into Human Nails and Implication in Treatment

Nail lesions are commonly caused by fungal and/or bacterial infections. Presently there are no effective drugs to treat them. This may be mainly attributed to inhibitory nature of the drugs, and slow diffusion of antibiotics into nail tissue. These two limiting factors can be easily overcome by the use of PG. First, PG at high concentrations is extremely powerful in killing bacteria and fungi (see below). Second, pure PG and 80% PG solution or gel, with or without salicylic acid or aluminum sulfate, were found to be rapidly absorbed into nails in adults; after 30 minutes of application of a thin layer to the surface of nails, virtually no PG can be found on the nail surface. Therefore, it is believed that PG at high concentrations alone or in combination with an astringent can be highly effective in treating various infection-related nail lesions.

Example 14

Extremely Powerful Microbicide of PG in High Concentrations

An 80% PG-20% water solution was prepared. Standard time-kill studies of the solution were conducted in three independent laboratories. At 1 minute, 99.99% of spiked *P. acne*, *P. aeruginosa*, *E. coli*, *S. aureus*, *C. albicans*, and *A. niger* were killed. Within 1 minute, the solution killed 99.9% of herpes simplex virus type 1 (HSV-1). A 40% PG-60% water solution killed 50% of HSV-1 within 1 minute.

Example 15

Markedly Enhanced Effects of PG Combined with Aluminum Salts in Acne Treatment

High concentrations (up to 88% used) of PG were highly effective against papular and pustular acne, but not effective against difficult-to-treat inflammatory nodular and cystic acne. In two adults with severe acne, preparations containing 65% PG and 12% aluminum zirconium tetrachlorohydrex glycine (AZTG) were found to be highly effective, flattening the acne lesions in about 3 to 7 days without any scarring. Remarkable efficacies were also observed when a gel of PG and aluminum sulfate was employed.

Example 16

Dramatically Enhanced Effects of Combination Formula in Canker Sore Treatment

Aqueous gels containing 55% PG and 0.8% aluminum sulfate were prepared using 2% Methocel as a gelling agent.

In the subject in Example 11, the gel was applied to the lesion site on three occasions around bedtime. After application, the subject reported that the irritation and pain stopped almost immediately, and that the lesion was completely gone by the next morning without any flare-ups on subsequent days. Complete healing after only one application was also observed in two other subjects. The above efficacy seems unprecedented since conventional medication takes several days to control the lesion.

Example 17

Enhancing Effects of Combination Formula in Wart Treatment

A male adult had two common warts on his hand. Daily application of a hydrogel containing 65% PG and 7% AZTG resulted in virtually complete removal of the warts within several weeks without any adverse effects. For conventional treatment with high strength salicylic acid, this removal process will usually take 6 to 12 weeks, and will leave an unsightly whitish film on the skin after each application.

Example 18

High Efficacy of Combination Formula in Insect Bites

Due to an insect bite, a male adult had a lesion (about 3 cm in length) on his ankle while experiencing swelling, inflammation, and itchiness. A liquid mixture containing 65% PG and 12% aluminum sulfate was applied to the lesion twice on the first day, and covered with a bandage. The itching subsided quickly and the lesion completely healed the next morning. No more applications were required. Healing of small, itchy skin lesions because of insect bites was observed in two subjects using the same formula.

Example 19

Dramatic Anti-Itch Effects of Combination Formula

A male adult had a chronic itching problem in the groin area of his leg and was not responsive to moisturizers. An aqueous gel containing 65% PG and 7% AZTG or 0.8% aluminum sulfate was found to almost immediately stop the itching. Furthermore, the effect of one application lasted for several weeks.

Example 20

Dramatic Results of Combination Formula in Treatment of Psoriasis

A female adult had plaque psoriasis for about 20 years and was frustrated with various drug therapies due to their serious side effects, high expenses, and rapid development of resistance to therapy. Gels containing high concentrations (greater than 50%) of PG with aluminum sulfate (5%) or AZTG (7%) were applied to her lesions twice a day. Itching stopped completely after the first day of treatment. Inflammation and redness was reduced substantially in the first week, and psoriasis was literally gone in the third month. There were no adverse effects and no resistance development over four months of daily use.

Example 21

Efficacy of Combination Formula for Nose Lesion

A male adult had an irritating, inflammatory, painful lesion near the orifice of his left nostril. A hydrogel containing 65% PG and 7% AZTG was applied twice with a cotton tip on the first day. The lesion symptoms completely disappeared the next day.

Example 22

Tick Bite Treatment

Tick bites can result in serious inflammation. Earlier, it was observed that use of a viscous liquid containing a weak antimicrobial agent, bismuth salicylate, was able to kill the invading tick after one application. In view of this, it is believed that a gel containing a high concentration of PG and an astringent should provide a method to treat tick bites.

Example 23

High Microbicidal Action of PG-Astringent Liquid Mixtures

A liquid mixture containing 65% PG, 2% salicylic acid, and 7% AZTG was found to kill 99.2%, 99.5%, and 99.9% of *P. acnes* at 1, 10, and 60 minutes, respectively.

Results of time-kill tests using a 30% PG-10% AZTG-60% water solution showed that at one minute 28%, 18%, 62%, 29%, and 12% of *P. aeruginosa*, *E. coli*, *S. aureus*, *C. albicans*, and *A. niger*, respectively, were killed, and at one hour 99.99% of all of them were killed.

It is to be understood that the above descriptions are intended to be illustrative, and not restrictive. One skilled in the art will be able to ascertain, without any more routine experimentation, many reference to specific embodiments described herein. These equivalents are intended to be encompassed by the following claims.

The subject matter of the U.S. patents, U.S. patent applications, and certain non-patent publications is hereby incorporated by reference in its entirety. In the event that an incorporated term or expression conflicts with a term or expression as defined herein, it is understood that the term or expression defined herein will control.

The invention claimed is:

1. A topical composition for treating skin lesions comprising:
    an anti-skin lesion agent consisting of from about 20% to about 99% by weight of propylene glycol and
    a pharmaceutically acceptable medium
    wherein the topical composition is to be applied to lesion sites as a thin layer at least once per day, and
    wherein the skin lesions are selected from the group consisting of herpes simplex, warts, shingles, nail infections, canker sore, cellulitis, folliculitis, scalp infections, hair infections, boils, gingivitis, periodontitis, impertigo, itch, psoriasis, eczema, dermatitis, and atopic dermatitis.

2. The composition of claim 1, wherein the concentration of propylene glycol ranges from about 25% to about 99% by weight.

3. The composition of claim 1, wherein the concentration of propylene glycol ranges from about 30% to about 99% by weight.

4. The composition of claim 1, wherein the concentration of propylene glycol ranges from about 40% to about 99% by weight.

5. The composition of claim 1, wherein the concentration of propylene glycol ranges from about 50% to about 99% by weight.

6. The composition of claim 1, wherein the concentration of propylene glycol ranges from about 60% to about 99% by weight.

7. The composition of claim 1, wherein the concentration of propylene glycol ranges from about 70% to about 99% by weight.

* * * * *